United States Patent
Ikonomidis et al.

(10) Patent No.: US 10,060,048 B2
(45) Date of Patent: Aug. 28, 2018

(54) METHOD FOR PREPARING HIGH QUALITY CRYSTALS BY DIRECTING IONIZED GAS MOLECULES THROUGH AND/OR OVER A SATURATED SOLUTION COMPRISING A PROTEIN

(71) Applicants: WMCS TECHNOLOGIES LIMITED, Hong Kong (CN); Kyriakos Ikonomidis, Athens (GB); Konstantinos Poulas, Patras (GR); Ioannis Tzimas, Trikala (GR)

(72) Inventors: Kyriakos Ikonomidis, Athens (GB); Konstantinos Poulas, Patras (GR); Ioannis Tzimas, Trikala (GR); John F. Wetling, Hundested (DK)

(73) Assignee: Wetling IP CCG Ltd, Tortola (VG)

( * ) Notice: Subject to any disclaimer, the term of this patent is extended or adjusted under 35 U.S.C. 154(b) by 180 days.

(21) Appl. No.: 14/438,448

(22) PCT Filed: Oct. 25, 2013

(86) PCT No.: PCT/EP2013/072418
§ 371 (c)(1),
(2) Date: Apr. 24, 2015

(87) PCT Pub. No.: WO2014/064260
PCT Pub. Date: May 1, 2004

(65) Prior Publication Data
US 2015/0284874 A1    Oct. 8, 2015

Related U.S. Application Data

(60) Provisional application No. 61/718,211, filed on Oct. 25, 2012.

(30) Foreign Application Priority Data

Oct. 25, 2012  (EP) .................................... 12189972

(51) Int. Cl.
C30B 7/12   (2006.01)
C30B 30/02  (2006.01)
(Continued)

(52) U.S. Cl.
CPC ............ *C30B 30/02* (2013.01); *C12N 9/2462* (2013.01); *C30B 7/00* (2013.01); *C30B 29/54* (2013.01);
(Continued)

(58) Field of Classification Search
CPC .... C30B 7/00; C30B 7/12; C30B 7/14; C30B 29/00; C30B 29/54; C30B 29/58;
(Continued)

(56) References Cited

U.S. PATENT DOCUMENTS

2005/0256300 A1   11/2005 Garetz et al.
2009/0081109 A1*  3/2009 Einav .................... C30B 29/406
                                                     423/409

(Continued)

FOREIGN PATENT DOCUMENTS

WO        0302506       2/1989
WO     WO2005021841     3/2005

(Continued)

OTHER PUBLICATIONS

Z. Hammadi, et al. "New approaches on crystallization under electric fields," Progress in Biophysics and Molecular Biology, vol. 101, pp. 38-44 (2009).*
Moreno, et al. publication entitled "The use of a new ad hoc growth cell with parallel electrodes for the nucleation control of lysozyme," Journal of Crystal Growth, vol. 264, pp. 438-444 (2004).*
Moreno, et al. publication entitled "The use of a new ad hoc growth cell with parallel electrodes for the nucleation control of lysozyme," Journal of Crystal Growth, vol. 264, pp. 438-444 (2004). (Year: 2004).*

(Continued)

*Primary Examiner* — Kenneth A Bratland, Jr.
(74) *Attorney, Agent, or Firm* — McHale & Slavin, P.A.

(57) ABSTRACT

Disclosed is a method for facilitating preparation of high quality crystals suitable for X-ray crystallographic studies. The method comprises that an electric charge or current is provided to a saturated solution of the molecule to be (Continued)

Figure 1:
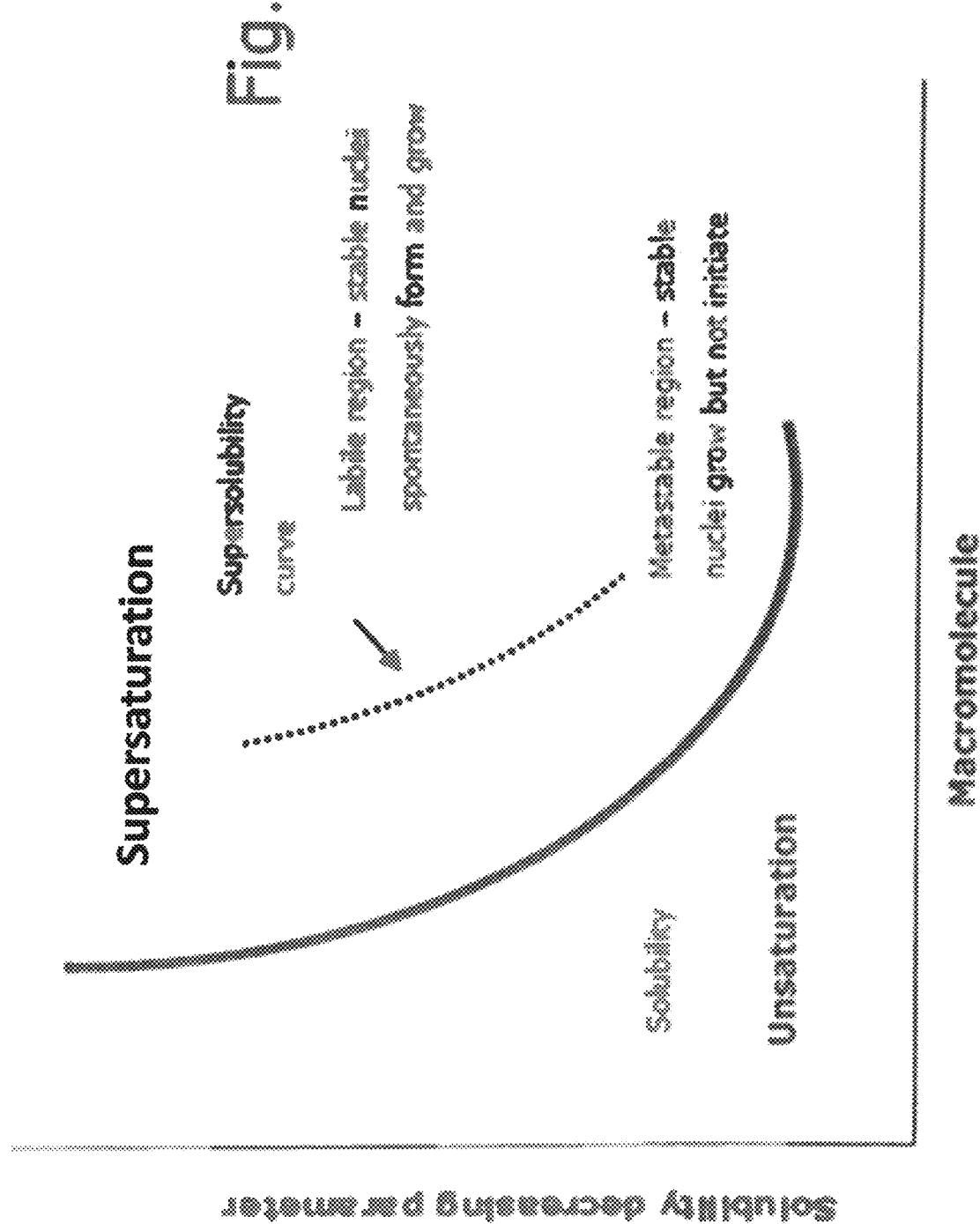

crystallized, preferably via a jet of gaseous ions. Also disclosed is an assembly for carrying out the method of the invention.

17 Claims, 7 Drawing Sheets

(51) Int. Cl.
 C30B 7/00 (2006.01)
 C30B 29/58 (2006.01)
 C30B 29/54 (2006.01)
 C12N 9/36 (2006.01)
(52) U.S. Cl.
 CPC ...... *C30B 29/58* (2013.01); *C12Y 302/01017* (2013.01)
(58) Field of Classification Search
 CPC ....... C30B 30/00; C30B 30/02; C12N 9/2462; C12Y 302/01017
 USPC .......................................... 117/11, 68–69, 925
 See application file for complete search history.

(56) References Cited

U.S. PATENT DOCUMENTS

| | | | |
|---|---|---|---|
| 2011/0112522 A1* | 5/2011 | Wetling | A61N 1/44 606/32 |
| 2011/0308948 A1 | 12/2011 | Wakamatsu et al. | |

FOREIGN PATENT DOCUMENTS

| | | |
|---|---|---|
| WO | WO2007042029 | 4/2007 |
| WO | WO2009102978 | 8/2009 |

OTHER PUBLICATIONS

Hammadi, Z. et al, "New approaches on crystallization under electric fields", Progress in Biophysics and Molecular Biology, Pergamon Press, Oxford, GB, 101:1-3:38-44, XP026884108, (Nov. 1, 2009).

Poulas, K. et al, "Crystal structure of Fab198, an efficient protector of acetylcholine receptor against myasthenogenic antibodies", European Journal of Biochemistry, vol. 268, pp. 3685-3693, (2001).

Koizumi, H. et al, "Control of effect on the Nucleation rate for hen egg white lysozyme crystals under application of an external ac electric field", Langmuir, 27:13:8333-8338, (2011).

Taleb, M. et al, "Crystallization of proteins under an external electric field", Journal of Crystal Growth, vol. 200:3-4: 575-582, (1999).

Taleb, M. et al, "Equilibrium kinetics of lysozyme crystallization under an external electric field", Journal of Crystal Growth, 232:1-4: 250-255, (2001).

Penkova, A. et al, "Enhancement and suppression of protein crystal nucleation due to electrically driven convection", Journal of Crystal Growth, vol. 275, pp. e1527-e1532, (2005).

Hou, D. et al, "ac field enhanced protein crystallization", Applied Physics Letter, vol. 92, pp. 223902, (2008).

Mcpherson, A., "Current approaches to macromolecular crystallization", European Journal of Biochemistry, vol. 189, pp. 1-23, (1990).

Mcpherson, A. et al, "Crystalization of biological macromolecules", Spring Harbor Laboratory Press, New York, Chapter 5, pp. 159-214, (1999).

Mcpherson, A. et al, "Crystalization of biological macromolecules", Spring Harbor Laboratory Press, New York, Chapter 6, pp. 215-269, (1999).

Mcpherson, A. et al, "Crystalization of biological macromolecules", Spring Harbor Laboratory Press, New York, Chapter 7, pp. 271-329, (1999).

* cited by examiner

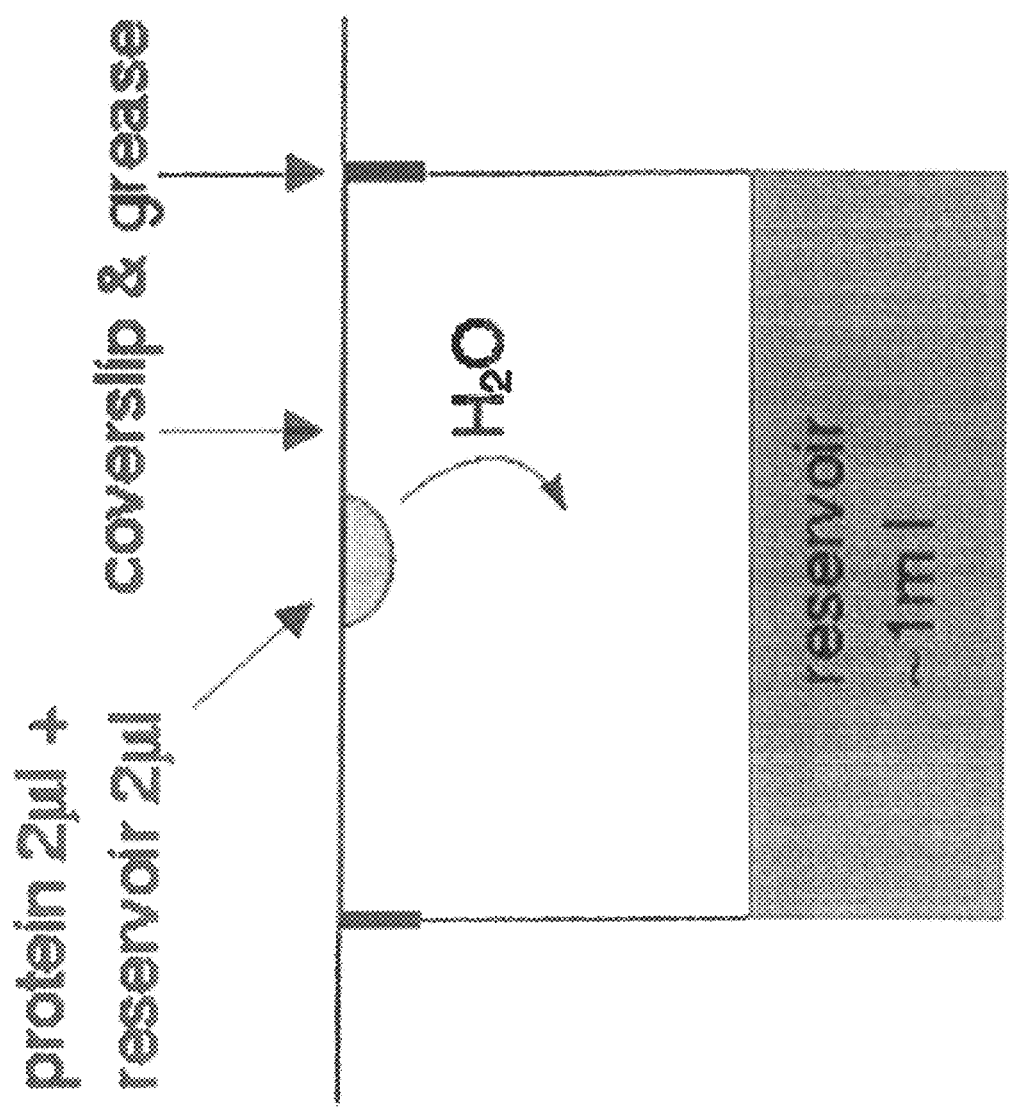

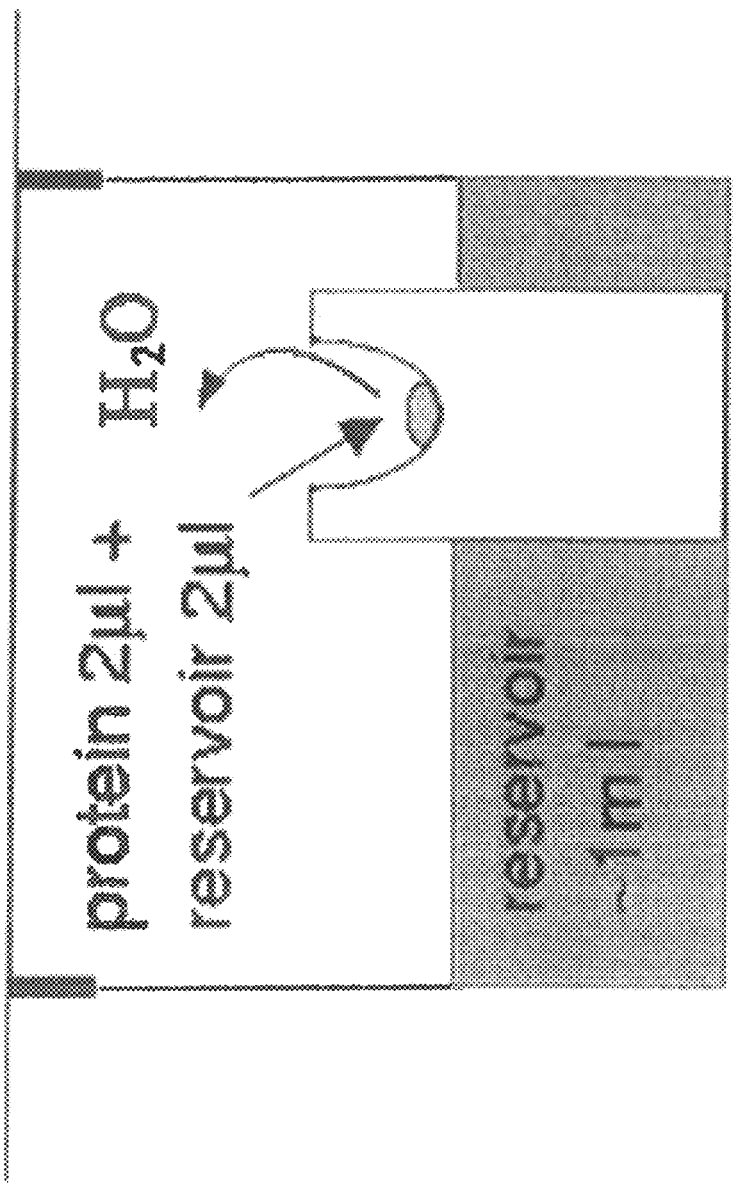

METHOD FOR PREPARING HIGH QUALITY CRYSTALS BY DIRECTING IONIZED GAS MOLECULES THROUGH AND/OR OVER A SATURATED SOLUTION COMPRISING A PROTEIN

CROSS REFERENCE TO RELATED APPLICATIONS

This is a national stage filing in accordance with 35 U.S.C. § 371 of PCT/EP2013/072418, filed Oct. 25, 2013, which claims the benefit of the priority of European Patent Application No. 12189972.8, filed Oct. 25, 2012 and U.S. Provisional Patent Application No. 61/718,211, filed Oct. 25, 2012, the contents of each are incorporated herein by reference.

FIELD OF THE INVENTION

The present invention relates to the field of provision of high-quality crystals suitable for e.g. X-ray crystallographic studies.

BACKGROUND OF THE INVENTION

Crystallization is the process of formation of solid crystals precipitating from a solution. It is also an industrial process; in chemical engineering crystallization occurs in a crystallizer. Crystallization is therefore an aspect of precipitation, obtained through a variation of the solubility conditions of the solute in the solvent, as compared to precipitation due to chemical reaction. Crystallization happens when atoms or molecules are arranged in a fixed lattice.

The importance of crystallization is that it serves as the basis for X-ray crystallography, wherein a crystallized molecule is used to determine the molecule's three-dimensional structure via X-ray diffraction. The first step in determining the structure of a molecule using X-ray crystallography is to grow crystals of sufficient quality to diffract X-rays strongly. X-ray crystallographic studies are of considerable interest to pharmaceutical and biotechnological industries, towards drug design and chemical engineering. By crystallizing and studying the molecules, one can understand mechanisms by which all the molecules function in biological systems. On the other hand, this knowledge can be useful in the ultimate development of new drugs.

Appropriate conditions for the production of crystals that produce a high-quality diffraction pattern must be found for each molecule before structure determination. However, since crystallization is relatively unpredictable, researchers have to perform a huge number of crystallization trials under various conditions. Molecules can be prompted to form crystals when placed in the appropriate conditions. In order to crystallize a molecule it undergoes slow precipitation from an aqueous solution. As a result, individual molecules align themselves in a repeating series of "unit cells" by adopting a consistent orientation.

Crystallization is a complex process, involving multiple equilibria between different states of the crystallizing species. The three stages of crystallization common to all molecules are nucleation, crystal growth and cessation of growth. During nucleation enough molecules associate in three dimensions to form a thermodynamically stable aggregate, the so called critical nucleus. These nuclei provide surfaces suitable for crystal growth, which can occur by a couple of different mechanisms. Crystal growth ceases when the solution is sufficiently depleted of spare molecules. Both crystal nucleation and growth occur in supersaturated solutions where the concentration of the crystallizing species, exceeds its equilibrium solubility value. The supersaturation requirements for nucleation and crystal growth differ.

The requirements for a molecule to crystallize are graphically described by the phase diagram as shown in FIG. 1.

In order to bring a molecule to the crystallization state there are different strategies, in general guiding the system to a state of reduced solubility. This can be achieved by changing one or more of many different parameters. A number of different parameters have been identified as affecting the crystallization process. Table 1 summarizes known parameters affecting crystallization.

TABLE 1

| CRYSTALLIZATION PARAMETERS | | |
|---|---|---|
| PHYSICAL FACTORS | CHEMICAL FACTORS | BIOCHEMICAL FACTORS |
| Temperature | Precipitant type | Sample purity |
| Methodology | Precipitant concentration | Macromolecular impurities |
| Time | pH and Buffer | Aggregation |
| Pressure | Ionic strength | Posttranslational modifications |
| Gravity, convection, sedimentation | Reducing/oxidizing environment | Sample source and storage |
| Vibrations/sound | Sample concentration | Proteolysis |
| Magnetic fields | Metal ions | Chemical and sequence modifications |
| Electric fields | Detergents | Sample symmetry |
| Dielectric properties | Small molecule impurities | Sample pI |
| Viscosity | Polyions | Sample history |
| Equilibration rate | Crosslinkers | Ligands and co-factors |
| Nucleants | Heavy metals | Contamination and impurities |
| Volume | Reagent source | Purification methodology |
| Particulate/amorphous material | Reagent purity | |
| Surface of crystallization device | Reagent formulation | |

A huge number of methods have been developed to investigate and influence prenucleation, nucleation and crystal growth. The nucleation of small molecules and macromolecules is governed by the same principles. In brief, in the supersaturation state clusters and aggregates of molecules are formed. If the dimensions reach a critical point (in other words if the radius of the clusters exceeds a certain size) then new molecules will accumulate more rapidly and the real nucleus will be generated. Different models have been proposed for the nucleation with the "Fluid Aggregate" model being the most appealing.

Figure 2:
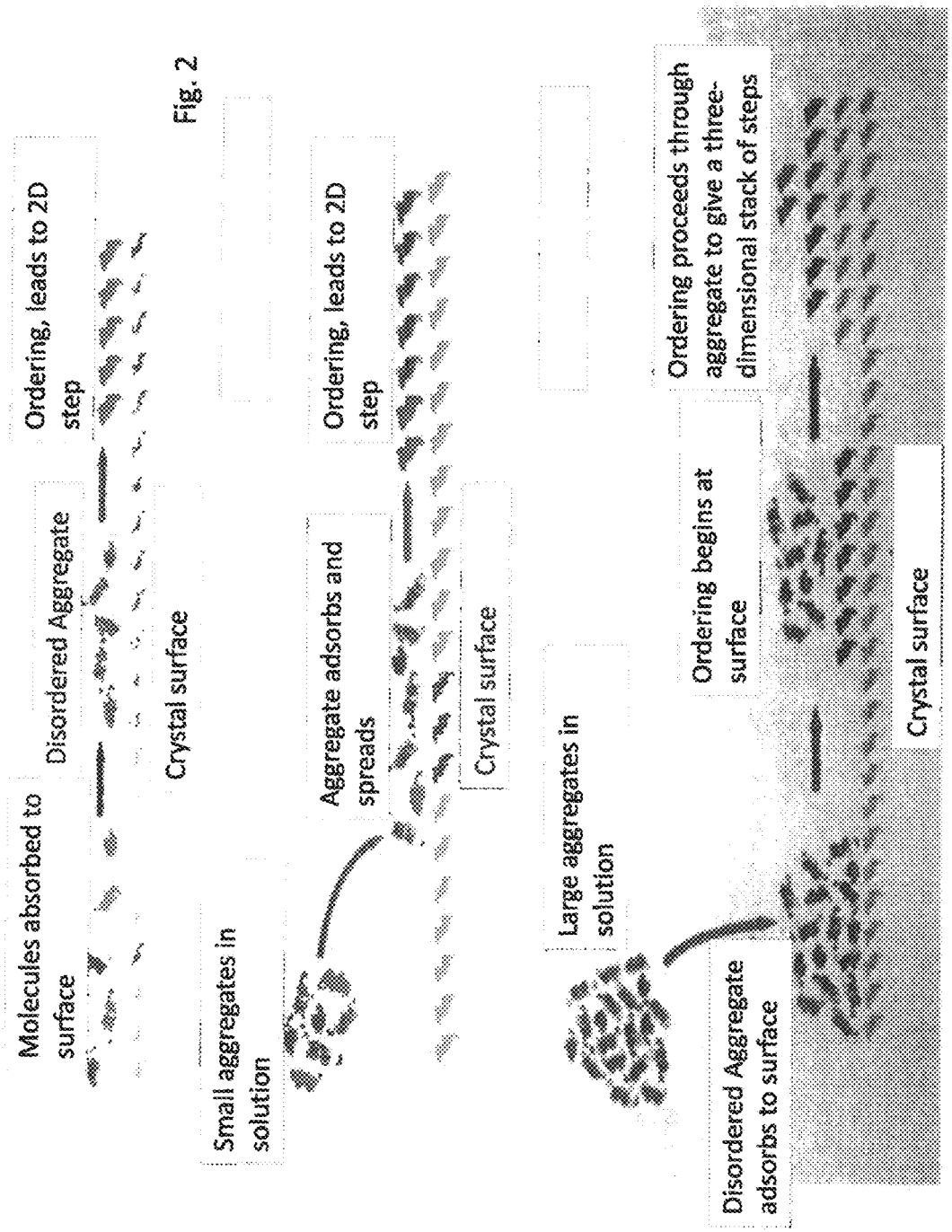

Crystal growth proceeds by direct addition and development of intact 3-D nuclei. FIG. 2 attempts to describe all the steps that drive the crystal growth process.

The crystal growth involves a number of interactions and bonds and is governed by complicated kinetics and thermodynamic laws.

Electric Fields and Crystallization

In solution, the molecules are surrounded by a hydration cage which hinders interactions between the molecules by acting as a dielectric and shielding the electrostatic attraction between adjacent molecules. Crystallization can only occur upon the removal of these hydration cages in supersaturated protein solutions. If this cage is removed too quickly by evaporation or an external field, however, the molecules will not reach their native conformation and the solution will form a gel instead. Existing methods such as vapor diffusion, seeding, microfluidics, electric fields, and magnetic fields hence aim to accelerate this slow diffusion and increase protein saturation in the solution to enhance crystal nucleation and growth. Z. Hammadi, Prog Biophys Mol Biol. 2009 November; 101(1-3):38-44 has reported that a localized, internal, electric field and direct current in agarose gel on the nucleation and growth of 2 biomolecules (one of which being Lysozyme) can control the whole nucleation process and can be used as a screening methodology. It is also proposed as a seeding technique for the crystal growth. The localized electric field was created by a nanometer size electrode tip, capable of generating an intense electric field.

H. Koizumi and collaborators, Langmuir 2011, 27:8333-8, have reported that an electric field can increase the nucleation rate of Hen Egg white lysozyme. In more details they have described a technique for the crystallization of proteins under the application of an AC electric field generated and controlled by an Electric Double Layer (EDL) which was formed at the inner surface of a protein solution drop immersed in low-density paraffin oil. Additionally, there are a large number of researchers who have tried to influence the crystallization process by electrostatic or current-injection fields. Taleb et al, 3. Cryst. Growth 1999, 200:575-82; Taleb et al, 3. Cryst. Growth 2001, 232: 250-55; Penkova et al, 3. Cryst. Growth 2005, 275:e1527-32 and many more have reported that a DC voltage, when applied to a protein solution (the protein being Lysozyme), was found to decrease the nucleation rate for all cases. On the other hand Hou and Chang, Appl. Phys. Lett. 2008, 92:223902, have reported the rapid increase in the crystal size of lysozymes by applying an AC current-injection field.

Methods of Crystallization

The conventional method of vapor diffusion, with either hanging or sitting drop, is usually adopted for the crystallization of the molecules. In this technique, a drop containing an amount of the molecule, stabilizing buffers, precipitants, and crystallization aids is allowed to equilibrate in a closed system with a much larger reservoir buffer. The reservoir usually contains the same chemicals, minus the molecule, but at an overall higher concentration, so that water preferentially evaporates from the drop; thus, it produces a gradual increase in molecule concentration and, under the right conditions, sometimes leads to the formation of crystals. Manual and automatic high-throughput approaches are used (in the lab or by commercial companies respectively).

A. Manual Crystallization Trials

Special hanging and sitting drop plates are used and a set of crystallization conditions is tested.

a. The wells of special 24-96 well crystallization plates are filled with 1 ml of various crystallization reservoir buffers (kits available with sets of 48 different crystallization buffers)

b. Drops (1-3 µl) of a concentrated molecule (2-50 mg/ml) are mixed with an equivalent volume of reservoir buffer and placed either on pre-siliconized cover slips (for hanging drop) or on special bridges (for sitting drop) so that the mix stays over the reservoir buffer (FIG. 3).

c. Plates are stored at different temperatures (4, 16, and 25° C.) and the wells are regularly inspected for crystal formation.

d. Formed crystals are tested to determine whether they are indeed formed of the molecule we wish (e.g. proteins are tested by Izit Crystal Dye, Hampton Research).

B. Crystallization Trials by Robotics

Crystallization robots have been developed to automate and speed up the experimental process of crystal growth. Crystal screening is also attempted using crystallisation robots provided as service by companies described as "structural genomics" companies (e.g. Structural GenomiX and Syrrx) or in-house. Crystallisation robots enable many crystallisations to be performed and minimise the amount of protein used. In fact, this system saves protein (50 nl instead of 1 µl sample per drop) thus allowing more screenings to be performed, saves time, and it is more reproducible. It is mainly used for the initial crystallization trials.

a. Sitting drop crystallization trials (50 nl protein+50 nl mother liquor) in 96-well plates. Each plate is imaged by conventional photonic microscope.

b. After identification of the proper crystallization conditions, trials are repeated by the manual approach and are further refined by slight modifications for the improvement of the crystal quality.

A list of relevant literature concerning crystallization is provided here:

1) A. McPherson, *Crystallization of biological macromolecules* (Spring Harbor Laboratory Press, New York, 1999).
2) P. C. Weber, *Overview of protein crystallization methods*, Methods in enzymology A 276 (1997)13.
3) A. McPherson, Review: current approaches to macromolecular crystallization, Eur. J. Biochem. 189 (1990) 1.
4) Poulas K, Eliopoulos E, Vatzaki E, Navaza J, Kontou M, Oikonomakos N, Acharya K R, and Tzartos S J (2001). Crystal structure of Fab198, an efficient protector of acetylcholine receptor against myasthenogenic antibodies. *Eur. J. Biochem.* 268: 1-10.

OBJECT OF THE INVENTION

It is an object of embodiments of the invention to provide means and methods for the optimization/improvement formation and growth of crystals, in particular of macromolecular compounds and complexes.

SUMMARY OF THE INVENTION

It has been found by the present inventor(s) that the application of electric charge (e.g. in the form of an electric current or of a build-up of electrostatic charge) in a macromolecule-containing solution via an externally administered jet, flux or stream of ionized gas, which provides for application of a net electric charge, is an effective means for establishing significant improvements in the crystallization ability of the macromolecules. Based on this finding, it has further been concluded that use of ionized gas molecules as a provider of electric charge is not necessarily the only means of achieving the improved results, since other "non-invasive" methods exist for charging a solution of a substance to be crystallized.

Hence, the present invention provides a method of using a jet, flux or stream of ionized gas molecules which carry a net electric charge ("wireless current") to cause the nucleation and/or crystal growth to occur or be facilitated and also to improve the diffraction quality of the crystals. As will be clear from the examples, there are circumstances where crystallization is not accomplished when using traditional crystallization techniques but where the application of gas ions has enabled the formation of useful crystals. This is the first report of a jet, flux or stream of ionized gas molecules which carry a net charge (wireless current) inducing nucleation and crystallization of molecules. The inventors have found that this may be an effect of inducing orientation of the polar molecules which are under crystallization, aiding them to get organized in a crystalline form. By applying the method of the invention it has been noted that the nucleation under the wireless current is different from the nucleation under identical conditions but in the absence of the wireless current. Additionally the nucleation with the use of the wireless current for various exposure times is different from the nucleation under identical conditions but in the absence of the wireless current. All the above are further supported by the finding that the crystals produced are of better diffraction quality than those produced without the wireless current exposure.

Further, while the application of an electric current via ionized gas molecules is a convenient way to obtain the improved crystallization effects, it is believed that similar effects will be attained if supplying electric charge or applying an electric current over or through a crystallization composition via other means that can mimic the establishment of a current supplied via an ionized gas. However, use of ionized gas has the specific advantage that charged particles can be delivered to the entire exposed surface of the crystallization solution while at the same time minimizing the risk of contamination of the solution. Further, in the embodiments where ionized gas is used primarily to build up an electrostatic charge in the crystallisation solution it is believed—without being limited to any theory—that the relatively small electrostatic charge that can be build up with ionized gas molecules provides for optimum crystallisation conditions. When projecting charged gas molecules onto the crystallisation solution it will become charged meaning that it will begin to repel gas molecules of the same polarity. Therefore, after a short while the continued projection of charged gas molecules towards the solution will result in an equilibrium where the charge of the crystallisation solution is maintained substantially constant at a not very high level.

So, in a first aspect the present invention relates to a method for preparing crystals of a substance, comprising
a) providing a net electric charge to a saturated solution comprising said substance, thereby facilitating crystal formation and/or crystal growth in said saturated solution and improving the diffraction crystal quality, or
b) establishing an electric current through and/or over said saturated solution comprising said substance, said electric current being established by directing a jet, flux or stream of ionized gas molecules, which carries a net electric charge, towards said saturated solution, thereby facilitating crystal formation and/or crystal growth in said saturated solution and improving the diffraction crystal quality, or
c) establishing an electric field in which a saturated solution comprising said substance is located, thereby facilitating crystal formation and/or crystal growth and improving the diffraction crystal quality in said saturated solution.

In a second aspect, the invention relates to a method for preparing crystals of a substance, comprising establishing an electric current through and/or over said saturated solution thereby facilitating crystal formation and/or crystal growth and improving the diffraction crystal quality in said saturated solution.

In a third aspect, the present invention relates to use of ionized gas molecules in the preparation of crystals.

In a fourth aspect the present invention relates to an assembly (or apparatus) suitable for preparing crystals of a substance, comprising
 a container that can accommodate at least one sample of
  a saturated or supersaturated solution of said substance,
 a gas ion transmitting device, which is adapted so as be
  capable of delivering a jet, flux or stream of ionised gas
  molecules that carries a net electric charge, and which
  is arranged relative to said container so that said jet,
  flux or stream of ionised gas molecules will be projected onto said saturated solution in said container,
 optionally an electrode, which is arranged relative to said
  containing so as to facilitate that said jet, flux or stream
  is projected towards with said saturated solution, and a
  conductor that connects said electrode to either said gas
  ion transmitting device or to ground, whereby an electric current can be carried via said ion transmitting
  device, said jet, flux or stream of ionized gas molecules,
  optionally said saturated solution, said electrode, and
  said conductor.

In a fifth aspect, the invention relates to an assembly (or apparatus) suitable for preparing crystals of a substance, comprising
 a container that can accommodate at least one sample of
  a saturated or supersaturated solution of said substance,
  said container being electrically insulated from its
  surroundings,
 an electrostatic generator, which is arranged so as to
  provide said container with a net electric charge.

LEGENDS TO THE FIGURE

FIG. 1: Phase diagram applying to crystal growth. The bold line (solubility curve) divides phase space into regions that support crystallization processes (supersaturation solutions) from those where crystals will dissolve (unsaturated solutions).

FIG. 2: The process of formation of 2- and 3-dimensional nuclei. In A monomers are associated to form a 2-D island. Later (B and C) aggregates give rise to multilayered stacks.

FIG. 3: Schemes illustrating crystallization methods. FIG. 3A shows the "hanging drop" crystallization method. B shows the sitting drop crystallization method.

FIG. 4: Schematic drawings of practical implementations of the present invention.
A: Implementation, where a discharge electrode has an area that exceeds the area of the wells in a microtiter system used for crystallization.
B: Implementation, where a discharge electrode has an area that does not exceed the area of the wells in a microtiter system used for crystallization.

Figure 5:
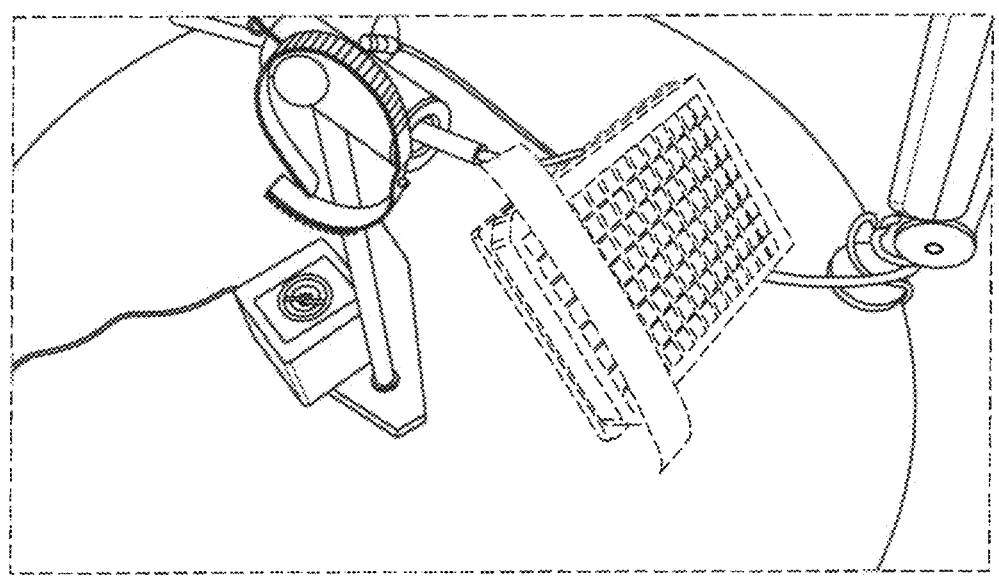

FIG. 5: Photograph of a practical implementation of the present invention.

DETAILED DISCLOSURE OF THE INVENTION

Definitions

Providing a "net electric charge" means that a sufficient amount of electric charge is provided to a site, whereby an electric current passes from said site to surrounding area for an appreciable period of time, or whereby an electrostatic charge is build up at said site. This means that a current has to be established for at least 1 second, but often longer, such as at least 10, 20, 30, 40, 50 or 60 seconds, or even at least several (2, 3, 4, 5, 6, 7, 8, 9, 10, 15, 20, 25, 30) minutes.

"Ionized gas molecules" broadly refers to gas molecules, which carry a net electric charge. Typical examples are negatively charged oxygen molecules ($O_2^-$) positively charged Nitrogen molecules ($N_2^+$) because of the abundancy of oxygen and nitrogen in atmospheric air, but any gas molecule capable of carrying a net charge is useful in the practice of the present invention. The important effect to achieve is simply that the jet, flux or stream provides the saturated composition with a net charge influx.

In the present specification and claims "a substance" denotes a molecule or assembly of molecules (e.g. a complex) which is capable of forming crystals. It is generally believed that the method of the invention will facilitate production of crystals from all kinds of substances, but it is contemplated that the present invention will be particularly useful in providing crystals of macromolecular compounds and macromolecular complexes (e.g. when crystallising or co-crystallising molecules with a view to obtain X-ray crystallographic data).

A "macromolecular compound" is a compound created by polymerization of smaller molecules and typically has a molecular weight in excess of 1 kDa. The term also embraces within its scope functional substances like multimeric proteins (which may be linked solely by non-covalent bonds and hence are normally considered to be multimers according to standard IUPAC terminology).

A "macromolecular complex" is a non-covalently linked complex between at least one macromolecular compound and another substance. Typical examples of interest are antibody-antigen complexes, complexes between receptors and ligands and also complexes between enzymes and known binding partners (e.g. competitive antagonists for the normal substrate of the enzyme).

"A saturated solution" is a solution where a substance is present in a maximum concentration under the ambient temperature and pressure, so that no further substance can be solubilised in said solution.

"A supersaturated solution" is a saturated solution where more of the dissolved substance is present than could be dissolved by the solvent under the solubility amount. Supersaturated solutions are prepared or result when some condition of a saturated solution is changed, for example when increasing temperature, decreasing volume of the saturated liquid (as by evaporation), or by increasing pressure.

The term "nucleic acid" denotes DNA and RNA, but also analogues thereof such as PNA and LNA.

A "gas ion transmitting device" is a device or apparatus, which is capable of generating a jet, flux or stream of ionized gas molecules having a net electric charge and where the direction of the jet, flux or stream may optionally may be controlled with respect to dosage, intensity and direction. Specifics concerning such devices are discussed below.

EMBODIMENTS OF THE INVENTION

As will appear from the examples, the present invention has been successfully used in the development of crystals under conventional conditions where crystals are not expected to appear and additionally has increased the incidence of crystallization, the total number of crystals that eventually appear and has improved the diffraction crystal quality.

This underscores that treatment with ionized gas molecules provides an effective means for facilitating crystallization and involves several advantages, since it is easy and practical to administer—further, the treatment of crystallisable solutions with ionized gas can in practice be combined with any means and method known in the art for preparing crystals. So, knowing from the prior art that ionic strength has been utilized successfully for the same scope, the present inventors have concluded that delivery of ionized gas molecules according to the teachings herein will be an advantageous improvement in other known technologies for crystal growth and crystallization.

The first aspect of the invention relates to a method for preparing crystals of a substance, comprising
a) providing a net electric charge to a saturated solution comprising said substance, thereby facilitating crystal formation and/or crystal growth in said saturated solution, or
b) establishing an electric current through and/or over a saturated solution comprising said substance, said electric current being established by directing a jet, flux or stream of ionized gas molecules, which carries a net electric charge, towards said saturated solution, thereby facilitating crystal formation and/or crystal growth and improving the diffraction crystal quality in said saturated solution, or
c) establishing an electric field in which a saturated solution comprising said substance is located, thereby facilitating crystal formation and/or crystal growth and improving the diffraction crystal quality in said saturated solution.

In embodiments of the first aspect of the invention, said substance is selected from the group consisting of a salt, an amino acid, a peptide, a protein, a carbohydrate, an amine, an alkane, an alkene, an alkyne, an aromatic compound, a heterocyclic compound, an alcohol, an organometallic compound, and a carboxylic acid. The invention has shown particular promise when crystallizing high MW molecules or complexes that notoriously may be difficult to crystallize, so it is preferred that the substance is a macromolecular compound, or complex. Typically, such a macromolecular compound is selected from the group consisting of a monomeric or multimeric protein; a nucleic acid; a polysaccharide; and a lipid, and typically the complex comprises a macromolecular compound, such as a complex of an antibody bound to an antigen or a receptor bound to a ligand.

According to the invention, the (super)saturated solution typically comprises a solvent selected from the group consisting of an organic, inorganic or supercritical solvent.

In the embodiments falling within option a) of the first aspect, that is, when the crystallization is facilitated by providing a net electric charge, the saturated solution should be electrically insulated from surrounding, so as to ensure that the charge provided will not discharge within a very short while. In these embodiments, the charge is typically delivered to said solution by means of a suitable device. For instance, a gas ion emitting device described in detail herein constitutes one advantageous possibility, but other means for delivering charge are believed to be equally useful. For instance, the group of devices known as electrostatic generators can be used; examples are a Van de Graaf generator, a Wimshurst machine, and a pellotron. Alternatively the device can be a friction machine which uses the triboelectric effect. One possibility is to supply charge from one of these devices where a container comprising the solution to be crystallized is connected to the terminal where charge is delivered. In such a setup, the delivered charge will become substantially evenly distributed over the combined area of the terminal of the electrostatic generator and of the container.

When convenient the provision of electric charge is terminated or interrupted in the first aspect of the invention, which means that no more charge will be added. Over time, the solution will hence become electrically neutralized due to loss of charge to the surrounding environment (for instance due to interaction with atmospheric air), but this may take considerable time. Typically, the termination or interruption is therefore accompanied or followed by a step of actively neutralizing the polarity of said saturated solution before the crystals obtained are processed further. This may be achieved by directly or indirectly grounding said saturated solution (contacting the container with a ground electrode if the container is made of a conductive material or by contacting the saturated solution directly with a ground electrode. Alternatively, the saturated solution can be subjected to ionized gas molecules of opposite polarity of the ionized gas molecules used to provide said net electric charge, for instance by supplying a jet, flux or stream of gas molecules in a mixture comprising both positively and negatively charged ionised gas molecules.

In interesting embodiments of the first aspect of the invention, option b) mentioned above is employed, that is, the crystallization is facilitated by establishing an electric current through and/or over said (super)saturated solution. This may according to the invention be achieved by providing the jet, flux or stream of gas ions from a gas ion transmitting device, which may in turn be connected to the (super)saturated solution via a discharge electrode (in this case a return electrode), thereby establishing an electric circuit—this enables a convenient way of controlling the administration of gas in response to the current that e.g. can be measured in the conductor between the return electrode and the ion transmitting device. Alternatively, the (super) saturated solution may simply be grounded (in this case the discharge electrode is not a return electrode)—in such a setup, the current that is led to ground may be used as input to control gas ion dosage. In both circumstances, the normal range of operation utilises a current of at least 0.1 µA and at most 100 µA, with typical values of at least 0.2, 0.3, 0.4, 0.5, 0.6, 0.7, 0.9, 1, 2, 3, 4, and 5 µA.

The ionized gas molecules (also termed "air ions") are hence conveniently provided from a gas ion transmitting device, which includes a gas ion generator (also known as an "air ionizer"). This type of device is known to the skilled person and is e.g. used in the semiconductor industry to counteract electrostatic charge building when handling and transporting microchips and wafers. However, a suitable gas ion transmitting device for use in the present invention is one which, apart from generating the ions, is capable of delivering a directed stream of gas ions having either a predominant positive or a predominant negative charge (where e.g. the devices used in the semiconductor industry typically deliver a balanced mixture of positive and negative ions).

In brief, such an apparatus generates a high voltage applied to an electrode, which thus produces an electric field that is most intense in a defined region (e.g. immediately adjacent a sharply pointed tip). The intense electric field disrupts the normal charge state of molecules of air gases (e.g. nitrogen and oxygen) in the region adjacent to the sharply pointed tip and some of the molecules become negative or positive ions, depending upon whether the molecule attains an excess or a deficiency of electrons (typically oxygen will become negatively charged, whereas nitrogen will become positively charged). The ions having a polarity opposite from the polarity of the high voltage of the electrode are attracted to the electrode and are neutralized, whereas ions of the same polarity as the high voltage electrode are repelled by the electrode and are dispersed outwardly. The subsequent projection towards the treated object with the thus generated air ions can be controlled when the receiving object is connected to a discharge electrode of opposite or neutral polarity (i.e. a ground electrode), which will ensure a correct projection of the ionized gas molecules in the desired direction towards the target area. Also, such a discharge electrode can be equipped with an amperemeter or other device for measuring the current passing through the electrode whereby the dosage of the ionized gas molecules can be controlled by a feed-back mechanism where gas ion generation and projection is controlled in response to the current passing through the discharge electrode (i.e. if the current exceeds a preselected current, the amount of gas ions projected by the ionized gas transmitting device is down-regulated, and vice versa).

Known suitable devices are disclosed in WO 2007/042029.

In embodiments of the first aspect of the invention, the net electric charge or electric current or electric field is provided until at least nucleation of crystals is expected to occur or until crystals are observed in said solution. However, longer durations of exposure may be advantageous in terms of crystal diffraction quality.

The net electric charge or electric current or electric field may be provided intermittently or constantly, e.g. a constant or intermittent DC current or wherein is applied a constant or intermittent AC current.

The nature of the ionized gas molecules are not believed to be critical, since it is their capability of carrying electric charge which is of highest relevance. However, it is practical that the ionized gas molecules when used in embodiments of the present invention are ions of molecules from atmospheric air. For instance they may be negatively charged gas ions, such as $O_2^-$ ions, or they may be positively charged gas ions such as $N_2^+$ ions.

In convenient embodiments, the jet, flux or stream of ionized gas molecules is projected directly onto said saturated solution. As mentioned above, this is often done at least until nucleation is expected to occur or until crystal formation is observed, but it is also possible to operate with fixed intervals of time. Typically, the jet, flux or stream of ionized gas molecules is applied for a period of time of at least 1 second, but substantially longer time may be necessary or practical—at least 10, at least 30, or at least 50 seconds, at least 2 minutes, at least 5 minutes, at least 10 minutes, at least 30 minutes, at least 45 minutes, at least 60 minutes, etc. In practice, the method may be carried out over several hours (at least 2, 3, 4, 5, 6, 8, 12, 15, 20) or even several (at least 2, 3, 4, 5, 6, 7, 8, 9 or 10) days.

The second aspect of the invention relates to a method for preparing crystals of a substance, comprising establishing an electric current through and/or over said saturated solution thereby facilitating crystal formation and/or crystal growth and improving the diffraction crystal quality in said saturated solution. In this aspect, the substance as well as the (super)saturated solution have the same characteristics as discussed in respect of the first aspect of the invention. When not using ionized gas for delivery of the electric current, the electric current can be established via at least one cathode and at least one anode, which are each in contact with said saturated solution and which are connected to an electrical power source, which in embodiments is adapted to deliver an electric current of at least 0.1 µA and at most 100 µA. As is also the case with the first aspect of the invention, the electric current is in some embodiments provided until at least nucleation of crystals has been observed in said solution, and it is also possible to provide the electric current intermittently or constantly, such as in the form of a constant or intermittent DC current or a constant or intermittent AC current. Also, the time for applying the current may be as discussed in respect of the first aspect of the invention.

In both the first and second aspects of the invention, crystallisation may further be facilitated by subjecting the saturated solution to any one of the following: cooling, heating, solvent evaporation, pressure change and solvent composition alteration.

The third aspect of the invention relates to use of ionized gas molecules in the preparation of crystals—it is to be understood that such use can incorporate all the features discussed in the context of the first aspect of the present invention.

Finally, the fourth aspect of the invention relates to an assembly suitable for preparing crystals of a substance, comprising
- a container that can accommodate at least one sample of a saturated or supersaturated solution of said substance,
- a gas ion transmitting device, which is adapted so as be capable of delivering a jet, flux or stream of ionised gas molecules that carries a net electric charge, and which is arranged relative to said container so that said jet, flux or stream of ionised gas molecules will be projected onto said saturated solution in said container,
- optionally an electrode, which is arranged relative to said containing so as to facilitate that said jet, flux or stream is projected towards with said saturated solution, and a conductor that connects said electrode to either said gas ion transmitting device or to ground, whereby an electric current can be carried via said ion transmitting device, said jet, flux or stream of ionized gas molecules, optionally said saturated solution, said electrode, and said conductor.

In other words, this assembly of the invention embodies the gas ion delivery related method of the first aspect of the invention in a practical setup, and therefore all features that characterize this part of the first aspect of the invention (choices pertaining to the substance, the saturated solution, the ionized gas molecules, the timing and form of gas ion delivery etc) apply mutatis mutantis to the fourth aspect of the invention. Consequently, the assembly of the invention is in certain embodiments one, wherein said ion transmitting device includes a control for setting said electric current and/or setting the timing of the delivery of said jet, flux or stream and/or setting the phase of said electric current and it is preferred that this is done so as to carry out the method of the first aspect of the present invention. For instance, it is preferred that the ion transmitting device is capable of delivering a jet, flux or stream of $O_2^-$ and/or $N_2^+$.

One practical embodiment is to have the control adapted so as to allow adjustment of said electric current in response to the electric current passing through the conductor. As mentioned above, this can result in two different modes of operation: if the saturated solution to be crystallized is insulated from the surroundings, the adjustment will serve to ensure a controlled projection of charged ions in the correct direction of the saturated solution thereby facilitating preservation of a stable electrostatic state, and if the saturated solution is in contact with the return electrode, the adjustment can directly control a gas ion generated current passing through or over the solution.

The fifth aspect of the invention relates to an assembly (or apparatus) suitable for preparing crystals of a substance, comprising
- a container that can accommodate at least one sample of a saturated or supersaturated solution of said substance, said container being electrically insulated from its surroundings,
- an electrostatic generator or a friction machine, which is arranged so as to provide said container with a net electric charge. The latter may, as explained above, be arranged relative to the container is such a way that the generator/friction machine has a terminal which accumulates the charge delivered by the device and that said terminal is in contact with the container and solution so as to allow charge to distribute itself over the combined area of the terminal and the container/solution. Useful electrostatic generators are described above.

The practical implementation of the inventive methods and assembly typically entails that a drop containing the molecules to be crystallized is exposed for a period of time to a jet, flux or stream of ionized gas molecules which carry a net charge sufficient to generate new crystallization nuclei or to increase the number of the already formed nuclei.

Figure 4A:
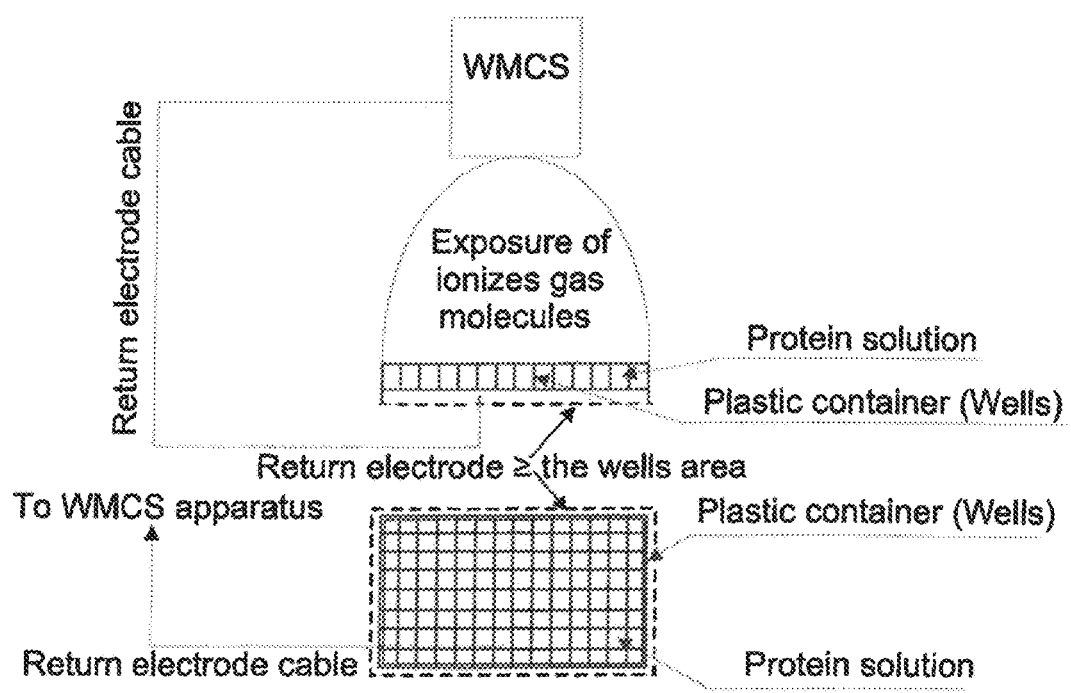
Figure 4B:
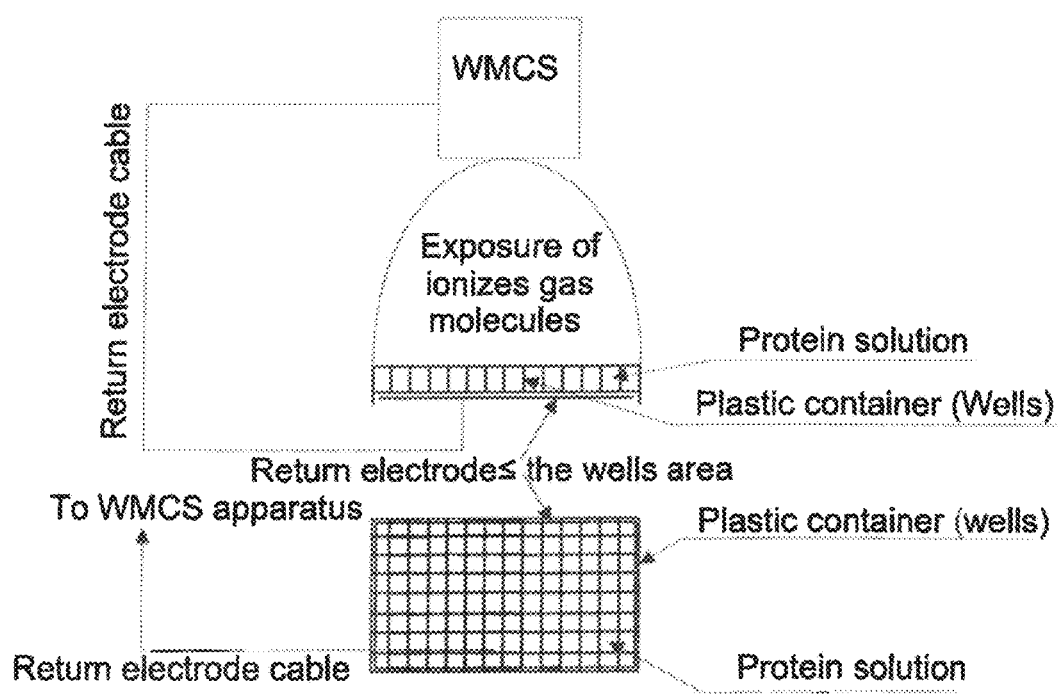

One set up system for both investigation of the influence of wireless current on the crystals and for implementation of the method of the invention is schematically shown in FIGS. 4A and 4B. A container (e.g. an open multi-well (8-96) plate with sitting or hanging droplets) comprises the molecules to be crystallized is subjected to a jet, flux or stream of gas ions from a gas ion transmitting device ("WMCS" in the figure). The plate is connected to a discharge electrode situated under the container. A control system operates by adjusting the flow of ions in response to the current returned from the discharge electrode. In some embodiments, the discharge electrode is arranged so as to be electrically insulated relative to (super)saturated liquid in the plate—in those embodiments, the discharge electrode mainly serves as a means for accurately directing the gas ions towards the plate so that an electrostatic charge can be provided. In other embodiments, the discharge electrode is in direct contact with the liquid, thus enabling the establishment of a current in a closed circuit consisting of the ion emitting device, the gas ions, the solution to be crystallised, the electrode and a conductor from the electrode to the ion emitting device.

FIG. 5 shows a picture of an experimental setup, where a gas ion emitting device is located on a table and a non-conducting polysterene multi-well plate is suspended and attached to a return electrode. In this setup, the gas ions emitted by the device will be directed to the multi-well plate and charged ions will be distributed over the surface. Thus in this setup, there is not established any current through or over the crystallisation solution present in the wells—rather, the continuous delivery of gas ions that are targeted towards the plate by the return electrode will cause a slight accumulation of charge on the plate surface and any loss of charge over time to the surroundings will be compensated by the delivery of gas ions.

It is to be noted that the use of a discharge electrode is truly optional, albeit practical. If situating the gas ion emitting device optimally relative to the crystallisation solution and the plate or container comprising it, the delivery of gas ions will be sufficient to provide the necessary charge distribution.

These setups allow investigation into the effect of the wireless current on the crystallization process of a macromolecule or macromolecular complex. In the Example referenced below, crystallization was investigated using a model protein, Hen Egg White Lysozyme (HEWL). Charge carrying ions were dispensed over the suspension for 4 and 8 minutes (plate 2 and plate 3 respectively) and the crystal formation was visually checked by a conventional optical microscope. After the exposure to the ions plates were stored at room temperature. The results show that the crystal production and the crystal quality increases with the time of wireless current treatment cf. the Example for more detail.

Example 1

Crystallization of a Model Protein, HEWL

Hen egg white lysozyme (HEWL) was the second protein and the first enzyme ever studied by X-ray diffraction and is still the most widely used for crystal growth studies. HEWL is an enzyme which hydrolyzes polysaccharides in bacterial cell walls. It is composed of 129 amino acids and has a molecular weight, $M_R$, of 14,296 Da (Da=dalton=1.66×10-27 kg). Lysozyme is particularly attractive for crystal growth research, because detailed information exists on its thermophysical properties (contrary to the situation for many other proteins).

Crystallization Conditions:

A preparation of 75 mg/ml HEWL, in 0.1 M NaAc pH 4.8 was prepared. The precipitation buffer was constituted of 6.5% (w/v) NaCl and 0.1 M NaAc pH 4.8. The protein solution was diluted in 0.1 M NaAc pH 4.8 to obtain the other protein concentrations set forth in Table 1 below.

The crystallization droplets were formed automatically (by an Oryx4 robot) by mixing 1 µl of the protein solution with 1 µl of the precipitation buffer. Each condition was repeated 8 times. Table 1 summarizes the crystallization conditions tested.

TABLE 1

| Condition A | Condition B | Condition C | Condition D | Condition E | Condition F |
|---|---|---|---|---|---|
| HEWL 75 mg/ml | HEWL 50 mg/ml | HEWL 25 mg/ml | HEWL 12.25 mg/ml | HEWL 6.125 mg/ml | HEWL 3.062 mg/ml |

Three different plates were used, Plate 1 was left untreated in room temperature (constant 18° C.), Plate 2 was treated for 4 minutes according to the method of the present invention and then left at room temperature while Plate 3 was treated for 8 minutes according to the method of the invention and then left at room temperature. In both cases, the crystallisation solution was insulated relative to the discharge electrode.

Tables 2-4 summarize the results for each from plates 1-3, respectively.

TABLE 2

Results from plate 1

| Condition A | Condition B | Condition C | Condition D | Condition E | Condition F |
|---|---|---|---|---|---|
| 1st crystal appeared 1.5 hours later 101 total crystals appeared 1 day later | No crystals after 6 hours There were crystals 20 hours later (when droplets were observed) | 1st crystal appeared 4 days later 9 total crystals appeared 4 days later | No crystals | No crystals | No crystals |
| 101 crystals were present a week later | 22 total crystals appeared 1 day later 27 crystals were present a week later | 9 total crystals were present a week later | | | |

TABLE 3 results plate 2

| Condition A | Condition B | Condition C | Condition D | Condition E | Condition F |
|---|---|---|---|---|---|
| 1st crystal appeared 1.5 hours later | 1st crystal appeared 3 hours later | 1st crystal appeared 28 hours later | 1st crystal appeared 4.5 days later | No crystals | No crystals |
| 176 total crystals appeared 1 day later | 27 total crystals appeared 1 day later | 14 total crystals appeared 4 days later | 3 total crystals appeared 5 days later | | |

TABLE 3-continued results plate 2

| Condition A | Condition B | Condition C | Condition D | Condition E | Condition F |
|---|---|---|---|---|---|
| 176 crystals were a week later | 29 crystals were a week later | 14 total crystals were a week later | 3 total crystals were a week later | | |

TABLE 4 results plate 3

| Condition A | Condition B | Condition C | Condition D | Condition E | Condition F |
|---|---|---|---|---|---|
| 1st crystal appeared 0.5 hours later | 1st crystal appeared 2 hours later | 1st crystal appeared 20 hours later | 1st crystal appeared 4.5 days later | No crystals | No crystals |
| 225 total crystals appeared 1 day later | 55 total crystals appeared 1 day later | 18 total crystals appeared 4 days later | 11 total crystals appeared 5 days later | | |
| 225 crystals were a week later | 55 crystals were a week later | 18 total crystals were a week later | 11 total crystals were a week later | | |

In X-ray diffraction experiments, crystals were used for data collection. A great number of datasets was obtained. Lysozyme crystals grown according to the method of the invention were qualitatively better than those obtained by the conventional vapor-diffusion method (control crystals). We used four indicators:
1) the signal intensity on the high resolution shell,
2) the mosaicity of the crystals and
3) the $R_{merge}$ indicator
4) the resolution The exposed crystals displayed higher values regarding of signal intensity and resolution and lower ones regarding the mosaicity and the Rmerge. Specifically, the samples exposed for 1, 2, 3 or 5 minutes displayed the highest signal intensity and resolution values combined with the lowest mosaicity and Rmerge values. The samples exposed for more than 5 minutes produced crystals of the same—more or less—quality with the control crystals.

From the above experiments it is clear that, when droplets are exposed to a stream of ionized gas molecules (in this case $O_2^{-1}$) according to the present invention in the initial stages of the crystal formation and growth process, the number of crystals increases (Tables 3 and 4), compared to control experiments (Table 2, no exposure to ionized gas-carried current) in all the different protein concentrations and the crystal diffraction quality is improved.

Further, the number and the diffraction quality of the crystals formed is also increased when increasing of the time that the drops are exposed to the method of the present invention. One condition (12.25 mg/ml HEWL) provided no crystals from control droplets (without exposure to the present invention, cf. Table 1), while exposure of the droplets to the method of the invention resulted in the appearance of 3 (at 4 minutes of exposure time) and 11 (at 8 minutes of exposure time) crystals.

The invention claimed is:

1. A method for preparing crystals of a substance comprising
    establishing an electric current through and/or over a saturated solution comprising a protein, said electric current being established by directing a jet, flux or stream of ionized gas molecules, which carries a net electric charge, towards said saturated solution, thereby facilitating crystal formation and/or crystal growth and improving diffraction quality of the crystals in said saturated solution, where improved diffraction quality is measured in terms of higher signal intensity, higher resolution, lower mosaicity, and lower $R_{merge}$.

2. The method according to claim 1, wherein the protein is selected from the group consisting of a monomer and multimer protein.

3. The method according to claim 1, wherein said saturated solution is supersaturated.

4. The method according to claim 1, wherein said saturated solution comprises a solvent selected from the group consisting of an organic, inorganic or supercritical solvent.

5. The method according to claim 1, wherein is established an electric current through and/or over said saturated solution.

6. The method according to claim 1, wherein the jet, flux or stream of gas ions is provided by a gas ion transmitting device, which is optionally connected to said saturated solution via a return electrode, thereby establishing an electric circuit.

7. The method according to claim 5, wherein the electric current is at least 0.1 µA and at most 100 µA.

8. The method according to claim 1, wherein the net electric charge or electric current or electric field is provided until at least nucleation of crystals is expected to occur or until crystals are observed in said solution.

9. The method according to claim 1, wherein the net electric charge or electric current or electric field is provided intermittently or constantly.

10. The method according to claim 9, wherein a constant or intermittent DC current is applied or wherein a constant or intermittent AC current is applied.

11. The method according to claim 1, wherein said ionized gas molecules are ions of molecules from atmospheric air.

12. The method according to claim 1, wherein said electric charge or current is carried by negatively charged gas ions.

13. The method according to claim 12, wherein the negatively charged gas ions are $O_2^-$ ions.

14. The method according to claim 1, wherein said electric charge or current is carried by positively charged gas ions.

15. The method according to claim 14, wherein the positively charged gas ions are $N_2^+$ ions.

16. The method according to claim 1, wherein the jet, flux or stream of ionized gas molecules is projected directly onto said saturated solution.

17. The method according to claim 1, wherein the jet, flux or stream of ionized gas molecules is applied for a period of time of at least 1 second.

* * * * *